(12) United States Patent
Doerr

(10) Patent No.: US 8,209,014 B2
(45) Date of Patent: Jun. 26, 2012

(54) MEDICAL IMPLANT HAVING AT LEAST TWO DATA COMMUNICATION CHANNELS

(75) Inventor: Thomas Doerr, Berlin (DE)

(73) Assignee: Biotronik CRM Patent AG, Baar (CH)

(*) Notice: Subject to any disclaimer, the term of this patent is extended or adjusted under 35 U.S.C. 154(b) by 348 days.

(21) Appl. No.: 12/503,965

(22) Filed: Jul. 16, 2009

(65) Prior Publication Data
US 2010/0016924 A1    Jan. 21, 2010

(30) Foreign Application Priority Data
Jul. 17, 2008    (DE) .................. 10 2008 040 502

(51) Int. Cl.
A61N 1/00 (2006.01)
(52) U.S. Cl. .......................................... 607/32; 607/60
(58) Field of Classification Search .............. 607/30–32, 607/60
See application file for complete search history.

(56) References Cited

U.S. PATENT DOCUMENTS
6,497,655 B1    12/2002    Linberg et al.
2003/0041866 A1*    3/2003    Linberg et al. ................. 128/899
2005/0159787 A1    7/2005    Linberg et al.
2006/0212092 A1*    9/2006    Pless et al. ...................... 607/45

FOREIGN PATENT DOCUMENTS
EP    15 83 585 B1    10/2005
EP    16 84 172 A1    7/2006
WO    WO 0143823 A1    6/2001
WO    WO 03/095024 A2    11/2003

* cited by examiner

Primary Examiner — Scott Getzow
(74) Attorney, Agent, or Firm — Craig A. Fieschko, Esq.; DeWitt, Ross & Stevens, S.C.

(57) ABSTRACT

A medical implant has at least one interface for bidirectional wireless data exchange, a data memory, and a controller. The controller and interface perform a wireless data exchange with at least two different external devices, resulting in at least two different data communication channels, one channel being assigned to data communication with the programming device and a second channel being assigned to data communication with a central service center. The medical implant is also designed to receive control commands and/or messages over the second channel while the second channel is active, and to recognize received control commands and/or messages intended for a programming device, store them temporarily in a memory (if necessary), and forward them to a programming device via the first channel when the first channel is active.

15 Claims, 9 Drawing Sheets

MEDICAL IMPLANT HAVING AT LEAST TWO DATA COMMUNICATION CHANNELS

FIELD OF THE INVENTION

The invention relates to a medical implant, i.e., an implantable medical device, such as a heart pacemaker, a cardioverter/defibrillator, or the like.

BACKGROUND OF THE INVENTION

Medical implants today often have at least one data communication interface for wireless data exchange with at least one external device, e.g., a programming device, or a so-called patient device which serves as a relay station for data exchange with a central service center.

Programming and scanning of such an implant with the help of a programming device are well known. For example, medical implants such as heart pacemakers and/or cardioverters/defibrillators are often capable of recording physiological data, e.g., intracardiac electrocardiograms or the like, during operation and transferring these data to the programming device in the event of a scan by the programming device. Conversely, it may be possible to reprogram the control of the medical implant with the help of the programming device. This is usually done when a patient wearing the medical implant visits the attending physician. The short range of the wireless data transfer between the medical implant and the external programming device presupposes a close proximity between the implant and the programming device, which results in the patient and physician also confronting one another in such a follow-up examination by a physician. Wireless data exchange between the medical implant and the programming device takes place via a first data communication channel of the medical implant assigned to the programming device.

In addition to this direct data exchange between the medical implant and the programming device, many medical implants today are capable of wireless data exchange over a second data communication channel with an external device in the form of a patient device, which is in turn connected to a central service center. The data communication link between the patient device and the central service center may be hardwired and may also take place via the Internet, for example. Data obtained from the medical implant, e.g., physiological data or operating data, may also be exchanged with the central service center via the second data communication channel. Conversely, programming commands or control commands may also be transmitted from the central service center to the medical implant via the second data communication channel.

A separate interface is usually provided for the first data communication channel and the second data communication channel, so that such a medical implant has two data communication interfaces. However, it is also possible to provide the same interface for data communication over the first data communication channel and the second data communication channel.

SUMMARY OF THE INVENTION

An object of the invention is to improve upon the foregoing systems. The invention achieves this object with use of a medical implant having at least one interface for bidirectional wireless data communication, a data memory, and a controller connected to the interface and the data memory, such that the controller in combination with the interface is designed to perform a wireless data exchange with at least two different external devices. There are at least two different data communication channels, a first data communication channel being assigned to data communication with a programming device and a second data communication channel being assigned to data communication with a central service center. The medical implant is also designed to receive control commands and/or messages intended for the programming device via the second data communication channel while the second data communication channel is active, and to temporarily store any received control commands and/or messages in the memory, if necessary, and to relay them via the first data communication channel to the programming device when the first data communication channel is active.

The interface may serve as a shared data communication interface for both data communication channels, or a separate interface may be provided for each data communication channel.

The controller of the medical implant is designed so that it automatically recognizes control commands and/or messages that are received via the second data communication channel and are directed to the programming device. Accordingly, it ensures temporary storage, if necessary, as well as automatic transmission from the medical implant to the programming device as soon as the first data communication channel is active.

With such a medical implant, it is possible to transmit messages from the central service center to the respective attending physician, these messages then being displayed for the attending physician via his respective programming device. In addition, depending on the type of programming device, a programming device may also be prompted to automatically scan certain data from the implant, for example. In other words, there may be indirect programming of the programming device by the central service center, in which case the medical implant (optionally a respective patient device) functions as the relay station.

In this way, messages can be transmitted to the attending physician of the respective patient without the physician having to make contact actively with a central service center.

It is also possible to reliably forward all important information available in a central service center via a patient with an electronic implant to the follow-up care physician without the latter having to have access to the central service center. Furthermore, it is possible to control automatic functions of the programming device based on information set in the central service center, e.g., to prompt a firmware update in a defined serial number group within the context of the next follow-up.

Likewise, important messages from the manufacturer of electronic implants (e.g., safety advisories) can be transmitted to the follow-up care physician without having to identify the follow-up care physician.

A preferred version of the implant has at least two interfaces, the first interface being assigned to the first data communication channel for bidirectional wireless data exchange with a programming device, and the second interface being assigned to the second data communication channel for bidirectional wireless data exchange with a central service center.

An exemplary programming device for wireless data scanning and programming of a medical implant has an interface for bidirectional wireless data exchange with a medical implant, a data memory, a display, and a controller connected to the interface of the programming device, the display and the data memory. This controller is designed to differentiate data packets received via the interface and to process them at least to such an extent that data packets containing a text message lead to display of the text message on the display device of the programming device and data packets containing control commands or programming commands lead to execution of these control commands or programming commands.

The programming device may be designed to also exchange information with the central service center over another interface. For example, the physician may be informed when the data transmitted from the medical implant to the service center via the second data communication channel contains unusual events requiring the special attention of the physician. Likewise, software updates of the programming device may also take place over this additional interface. If the programming device does not have the additional interface mentioned above with the central service center, and/or if communication between the programming device and the central service center is impossible for various reasons, this information cannot be transmitted in known systems.

The programming device is preferably further designed to generate an acknowledgement of receipt directed at the respective central service center after receiving a data packet generated by a central service center and to transmit it to a medical implant via the first data communication channel.

In this context, the term "data packet" is to be understood as meaning that a respective data packet as mentioned herein may also be transmitted in the form of a plurality of data subpackets. Thus a data packet refers not only to an individual data subpacket such as that which occurs in the data transmission, depending on the transmission protocol.

The invention also includes a medical therapy system having an implant of the type described previously as well as a central service center, which is temporarily connected to the medical implant for data exchange via a data communication channel (the second data communication channel), where the central service center is designed to generate data packets with text messages and/or control commands and programming commands directed to a programming device to be connected to the medical implant, and to transmit them to the medical device when the (second) data communication channel is active. In this sense, a central service center, which is designed to generate data packets containing text messages and/or control commands and programming commands directed to a programming device to be connected to the medical implant, is an independent aspect of the invention. The central service center preferably has an interface for input of text messages intended for a programming device. In this way, a home monitoring physician connected to the central service center can generate messages to a follow-up care physician responsible for the follow-up care of an implant patient and can be certain that this follow-up care physician will receive the message at the proper point in time, namely when he establishes contact with a respective implant by means of a programming device.

On the whole, this yields a system having at least one electronic implant, a central service center and a programming device, such that the implant is preferably connected by a second data communication channel to the central service center, so it regularly sends information to the central service center via a relay station (i.e., a patient device and/or an external device) and conversely is able to receive and store information from the central service center. Such information stored in the implant may be read out by the programming device used in follow-up care if it is directed to the programming device and may be used for display or control of automatic responses of the programming device.

This yields the following advantageous variants of such a system and/or its system components (medical implant, programming device or central service center):

(a) The information transmitted from the central service center to the implant, which is then scanned and processed by the programming device of the follow-up care physician, is input manually into the central service center.

(b) The information transmitted from the central service center to the implant, which is then scanned and processed by the programming device of the follow-up care physician, is generated automatically in the central service center as the result of a data analysis.

(c) The information transmitted from the central service center to the implant, which is then scanned and processed by the programming device of the follow-up care physician, is transmitted to the central service center by means of a data transmission interface of the manufacturer of the implants (e.g., serial number lists with the respective firmware versions).

(d) The information transmitted from the central service center to the implant is used in a scan by the programming device to control the programming device.

(e) The information transmitted from the central service center to the implant is used in a scan by the programming device to control a firmware update of the implant firmware.

(f) The information transmitted from the central service center to the implant is used in a scan by the programming device for automatic reprogramming of at least one parameter of the electronic implant.

(g) The scan of the information transmitted by the central service center to the electronic implant by the programming device is acknowledged by the programming device, and this acknowledgement is then transmitted with the periodic message to the central service center.

BRIEF DESCRIPTION OF THE DRAWINGS

Exemplary versions of the invention will now be explained in greater detail with reference to the figures, in which.

DETAILED DESCRIPTION OF PREFERRED VERSIONS OF THE INVENTION

Figure 1:
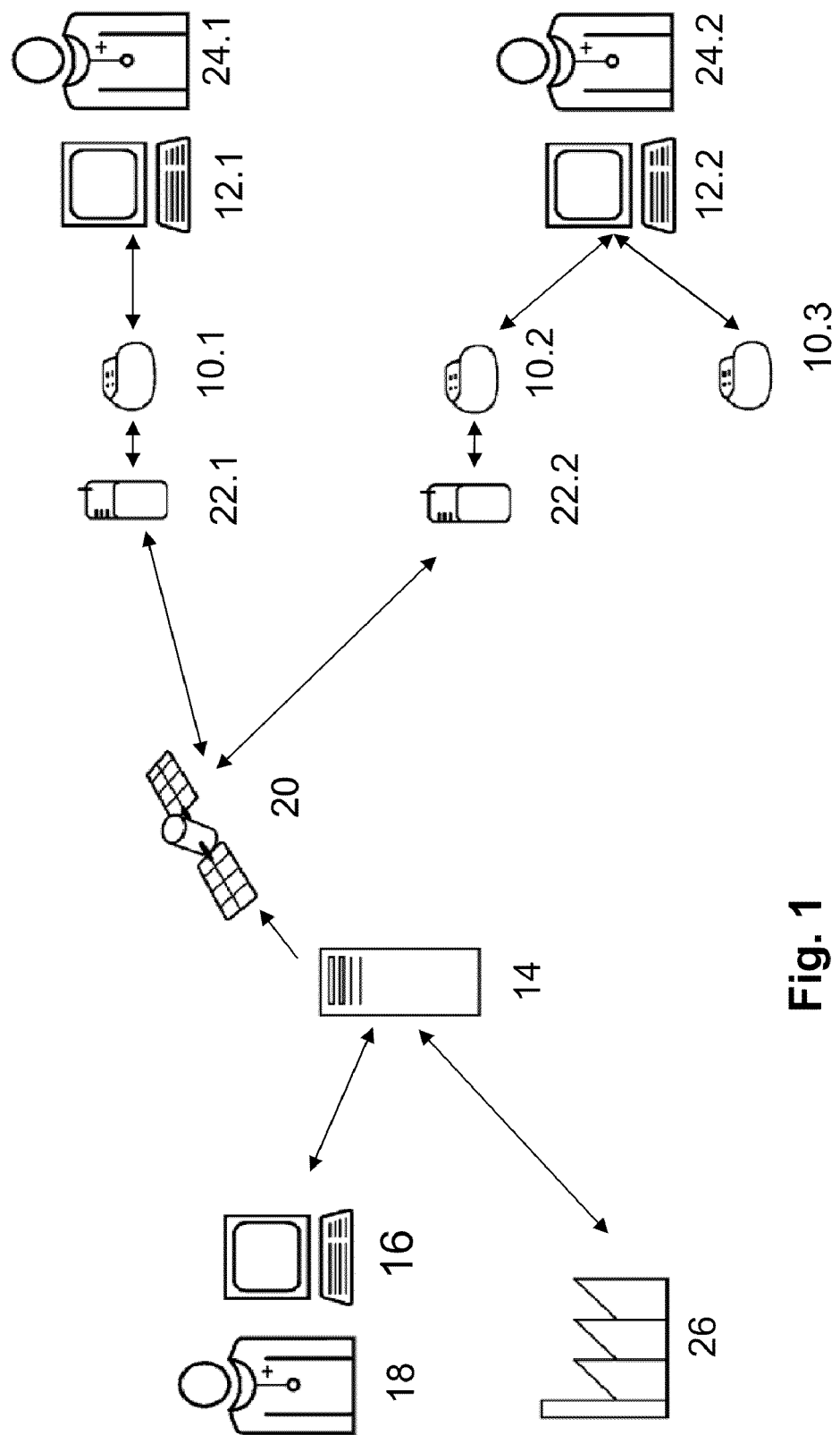
FIG. 1: shows a medical therapy system having the inventive implant, an inventive programming device and an inventive central service center.

FIG. 1 shows an overview of an inventive therapy system including an inventive medical implant 10, a programming device 12 assigned to the implant 10 and a central service center having a server 14. For a better understanding, the diagram includes several medical implants 10, shown as 10.1, 10.2, 10.3, plus several programming devices 12, shown as 12.1 and 12.2, plus several patient-individual relay stations 22, shown as 22.1 and 22.2, as well as several follow-up care physicians 24, shown as 24.1 and 24.2. For the functioning of the inventive therapy system, the use of only one of this components shown in multiple forms is sufficient The server 14 is connected to a terminal 16 by which a physician 18 has access to the server 14 for remote monitoring of implants 10. The server 14 communicates via a communication link 20 with multiple patient-individual relay stations 22 which are the aforementioned patient devices, for example. These in turn communicate with a respective electronic implant 10 of a patient. The data link between the server 14 and the respective implant 10 via the respective relay stations 22 forms a second data communication channel, while a data communication link between a respective implant 10 and a respective programming device 12 forms a first data communication channel. The two data communication channels are not usually active continuously but instead are active only temporarily if for no other reason than to save on transmission energy on the part of the implant 10.

At periodic intervals, the electronic implants 10 are scanned by follow-up care physicians 24 via a respective programming device 12 and are reprogrammed if necessary. This takes place via the first data communication channel. Electronic implants 10 which do not have any connection to the server 14 of the central service center are also regularly scanned in this manner. Such an electronic implant is shown as 10.3. In a preferred version of the overall system, the manufacturers 26 of the respective electronic implant 10 also have access to the server 14 of the central service center to thereby allow remote monitoring of the electronic implants 10 by the respective manufacturer 26.

Figure 2:
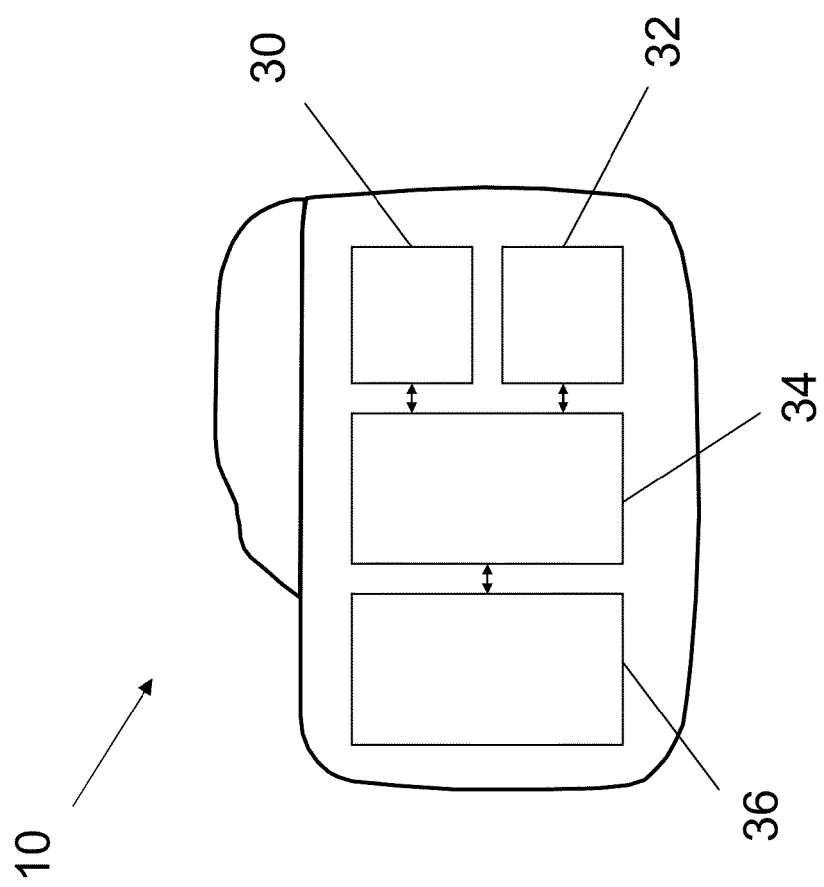
FIG. 2: shows a schematic diagram of an inventive medical implant.

FIG. 2 shows that a typical inventive implant 10 has a first interface 30 and a second interface 32, both of which are connected to a control unit 34 and a memory 36. The first interface 30 is for bidirectional wireless communication with a programming device 12 (FIG. 1) and the second interface 32 is for bidirectional data communication with an external device, i.e., a patient device 22 (FIG. 1) as a relay station for bidirectional data communication with a central service center. Data generated by the implant 10 itself or data received by the programming device 12 or the central service center 14 may be saved in the memory 36. The control unit 34 is designed to recognize data packets generated by the central service center 14 and sent to a programming device 12 and to save the data temporarily in the memory 36, if necessary, to forward them to a programming device 12 in the event of bidirectional data communication with a programming device 12.

Figure 3:
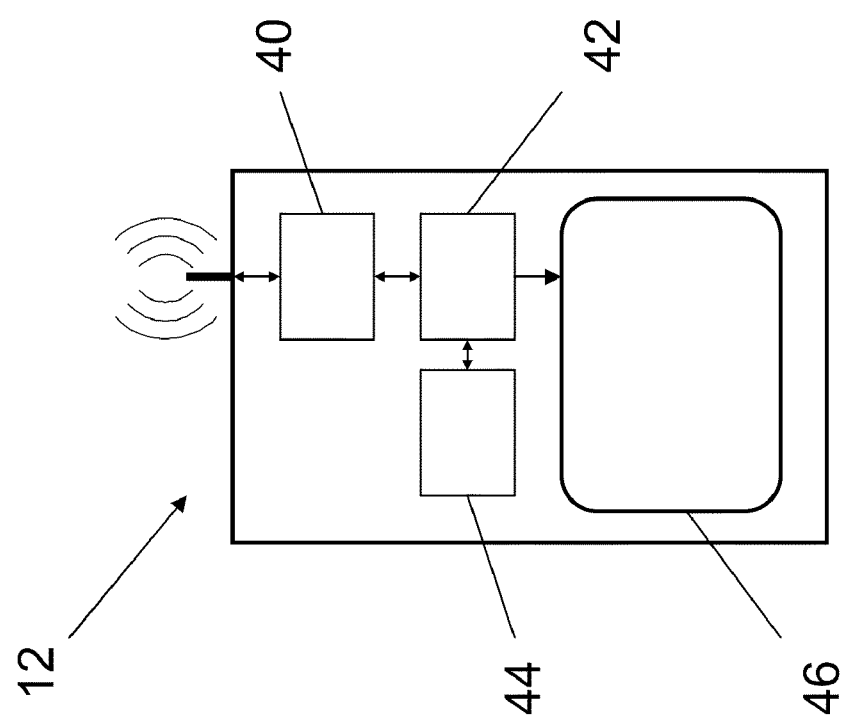
FIG. 3: shows a schematic diagram of an inventive programming device.

The programming device 12 illustrated in FIG. 3 has an interface 40 for bidirectional wireless data transfer between an implant 10 and the programming device 12. This interface 40 of the programming device 12 is connected to a control unit 42 of the programming device 12 and to a memory 44 of the programming device 12. The control unit 42 of the programming device 12 is also connected to a display 46 on the programming device 12. The display 46 may serve, for example, to display text messages or to display intracardiac electrocardiograms in a graphic display. Such intracardiac electrocardiograms are generated in an implant 10, for example, and are transmitted from the implant 10 to the programming device 12 when the implant 10 is scanned by the programming device 12.

The control unit 42 of the programming device 12 is additionally designed to recognize data packets received by the implant 10 that have been generated by a central service center 14 and contain text messages or control commands and programming commands for the programming device 12. Such data packets are decoded by the controller 42 of the programming device and then lead to a display of a text message, for example, on the display 46. In the case of control commands or programming commands, receipt of same may also prompt the controller 42 of the programming device 12 to perform certain scans of the implant 10, for example, or also to perform a firmware update of the programming device 12 itself.

Figure 4:
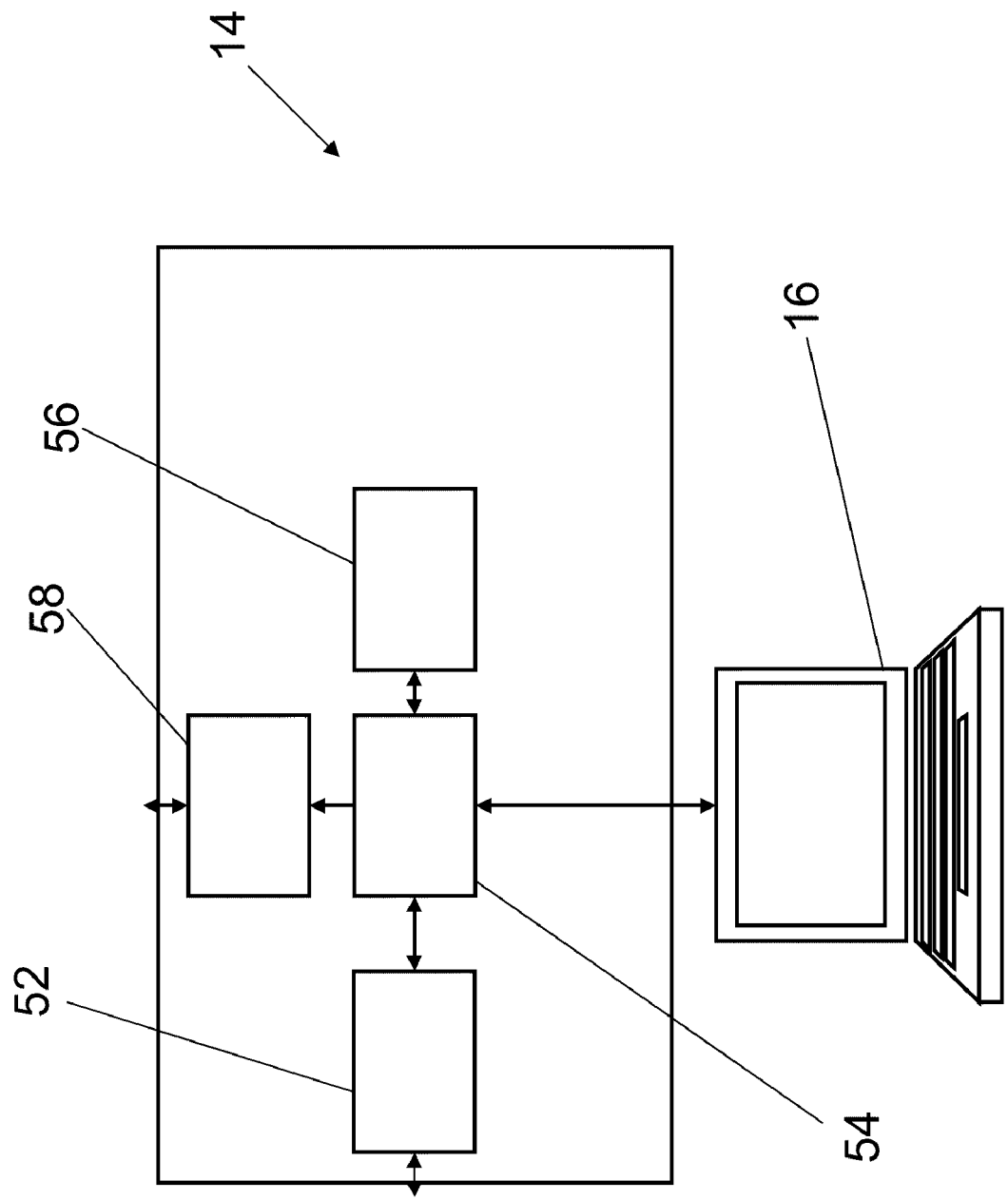
FIG. 4: shows a schematic diagram of an inventive service center.

The service center 14 illustrated in FIG. 4 includes an interface 52 for bidirectional data transmission between the server 14 and an implant 10, and also has a control unit 54 designed to generate data packets directed at a programming device 12 that is to be connected occasionally to the implant 10. To this end, the control unit 54 of the server 14 is connected to a terminal 16, for example, for input of such text messages or to an automatic analyzer unit 56 for analysis of data received by the implant 10, e.g., physiological data about a patient or operational data of an implant 10. In addition, the server 14 preferably has another interface 58 by which a manufacturer 26 of an implant 10 has access to the central service center 14.

Figure 5:
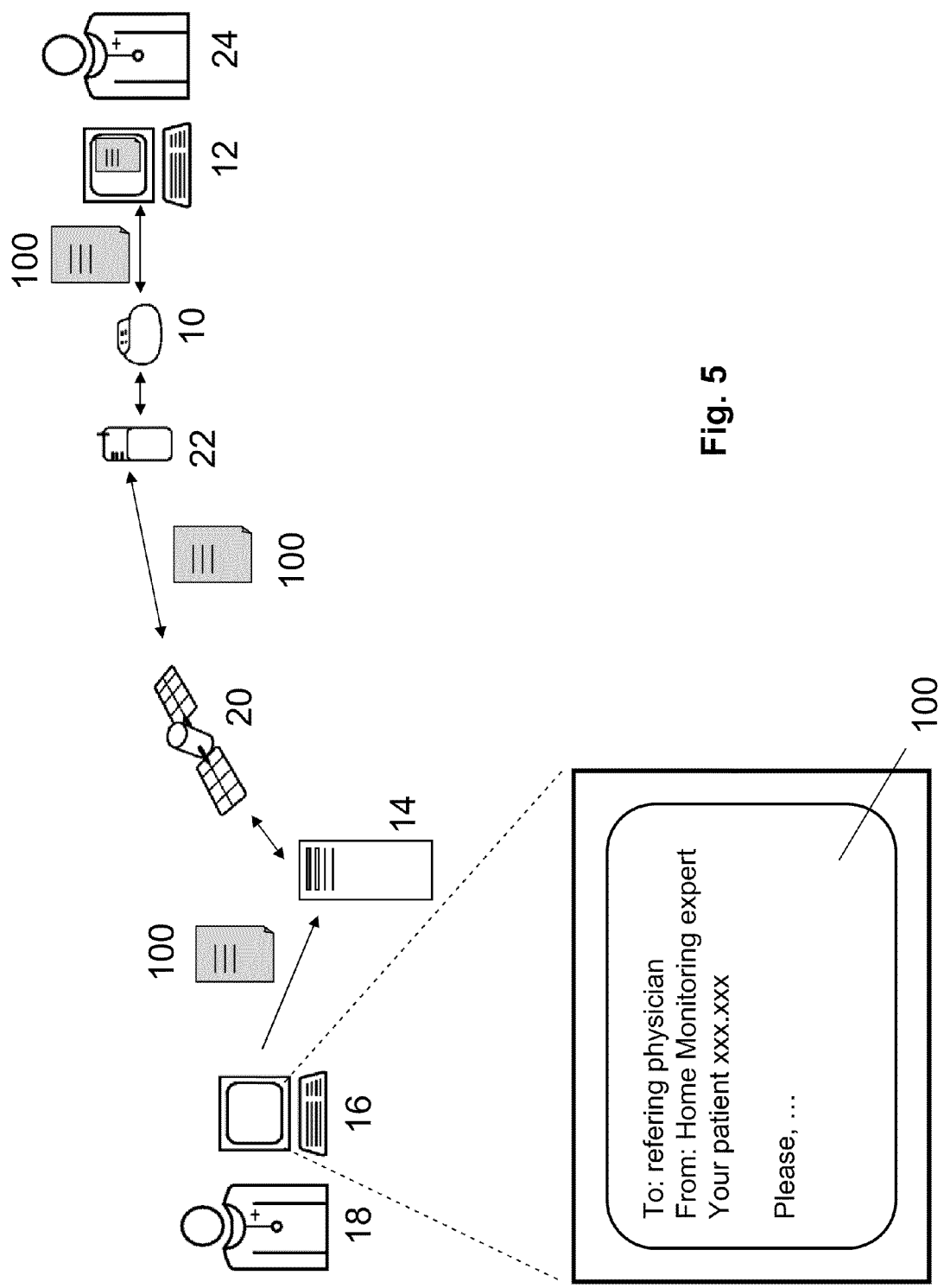
FIG. 5: shows the system from FIG. 1 in the case of information for a follow-up care physician by a home monitoring physician.

FIG. 5 shows an example of how data transmitted by the implant 10 to the central server 14 is analyzed by a specialized physician 18 at his terminal 16. This physician 18 then has an opportunity to prepare a text or voice message 100 on his terminal 16 for a follow-up care physician 24 who may have less expertise under some circumstances, and to send it to the server 14. This server 14 then sends the implant-specific message 100 automatically via the communication link 20 to the patient device 22. The patient device 22 then transmits the received information 100 to the electronic implant 10 with the next possible link between the electronic implant 10 and the patient device 22.

With regular follow-up care of this electronic implant 10 by the corresponding follow-up care physician 24, the message 100, which is stored in an area of the memory 36 in the implant 10 reserved specifically for this purpose, is then scanned by the programming device 12 and displayed on its display 46. The implant 10 thus functions more or less as a mailbox for the patient device 22.

The programming device 12 may optionally automatically or manually acknowledge receipt of a data packet or a message 100 by the follow-up care physician 24, and this information is then transmitted in the form of a data packet 100 generated by the programming device 12 to the implant 10, where it is stored in its memory 36. This acknowledgement of receipt is then sent via the patient device 22 and via the communication link 20 to the server 14, in the case of the next regular data communication between the implant 10 and the service center 14. The acknowledgment of receipt transmitted in this way may then be displayed for the remotely monitoring physician 18 on his terminal 16.

Figure 6:
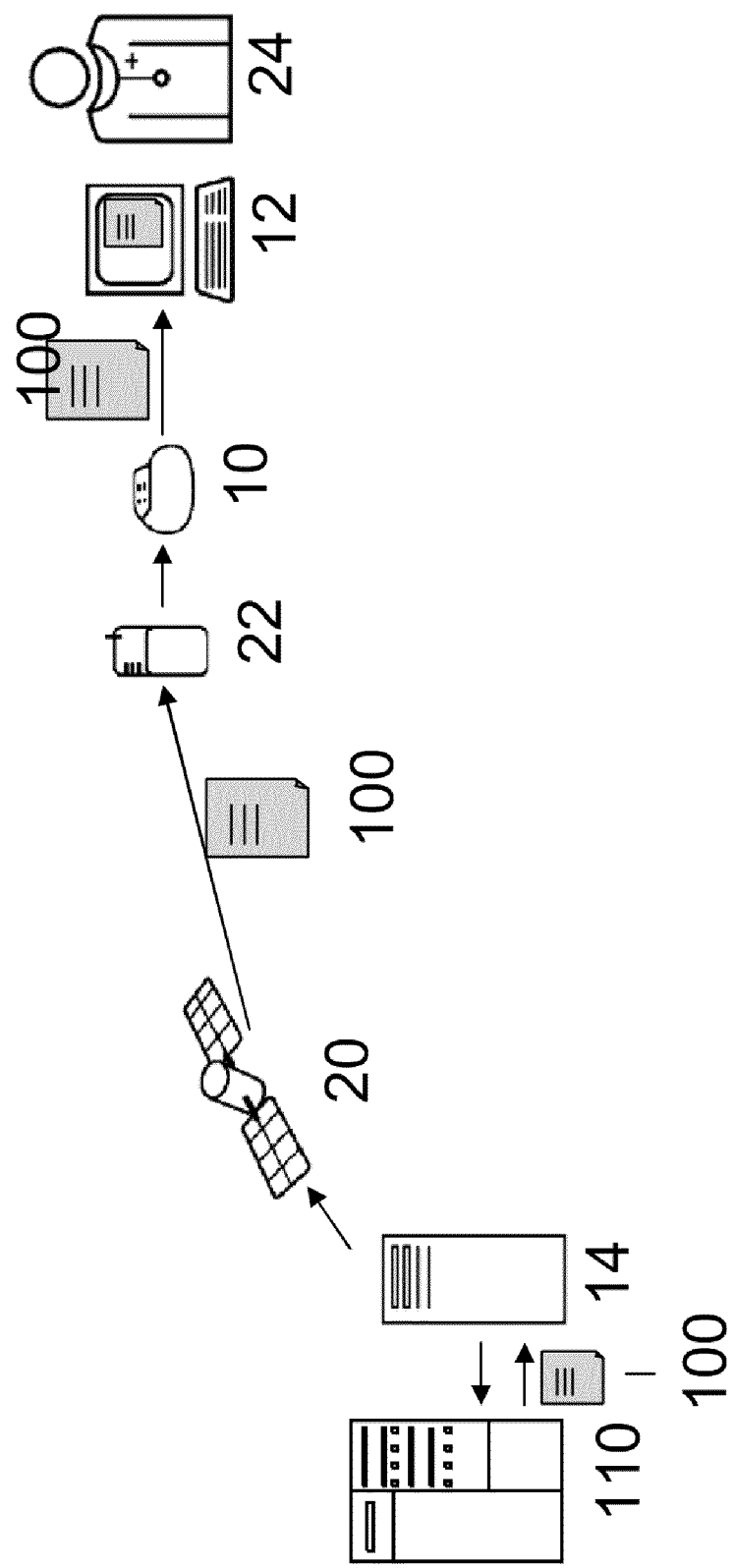
FIG. 6: shows the system from FIG. 1 in the case of automatic information from a follow-up care physician by an automatic analysis by the central service center.

In FIG. 6 the information for a follow-up care physician 24 is displayed by automatic analysis of data received from an implant 10 in the server 14. The data stored in the server 14 from an electronic implant 10 is automatically analyzed by analytical software in an analytical computer 110. When certain criteria are met, the analytical computer 110 automatically generates an "event report" 100. This event report 100 is sent in the form of an automatically generated data packet 100 from the analytical computer 110 to the server 14 and is then issued to (and saved in) the respective implant 10, via the communication link 20 and the patient device 22 via the second data communication channel.

In the event of follow-up care by a follow-up care physician 24, the latter can scan and inspect the event report 100 stored in the implant 10 with a programming device 12.

In this way it is possible to use far more complex automatic analytical algorithms for analysis of data generated by the electronic implant 10 than would currently be possible with an implant 10 or a programming device 12. In particular, it is possible in this way to process much more trend data, i.e., data of one or more parameters collected over a period of several years, for example, because the data are stored in the server 14 and not in the electronic implant 10. Likewise, the computation power of a typical analytical computer 110 is far greater than that of a programming device 12 or an implant 10.

Figure 7:
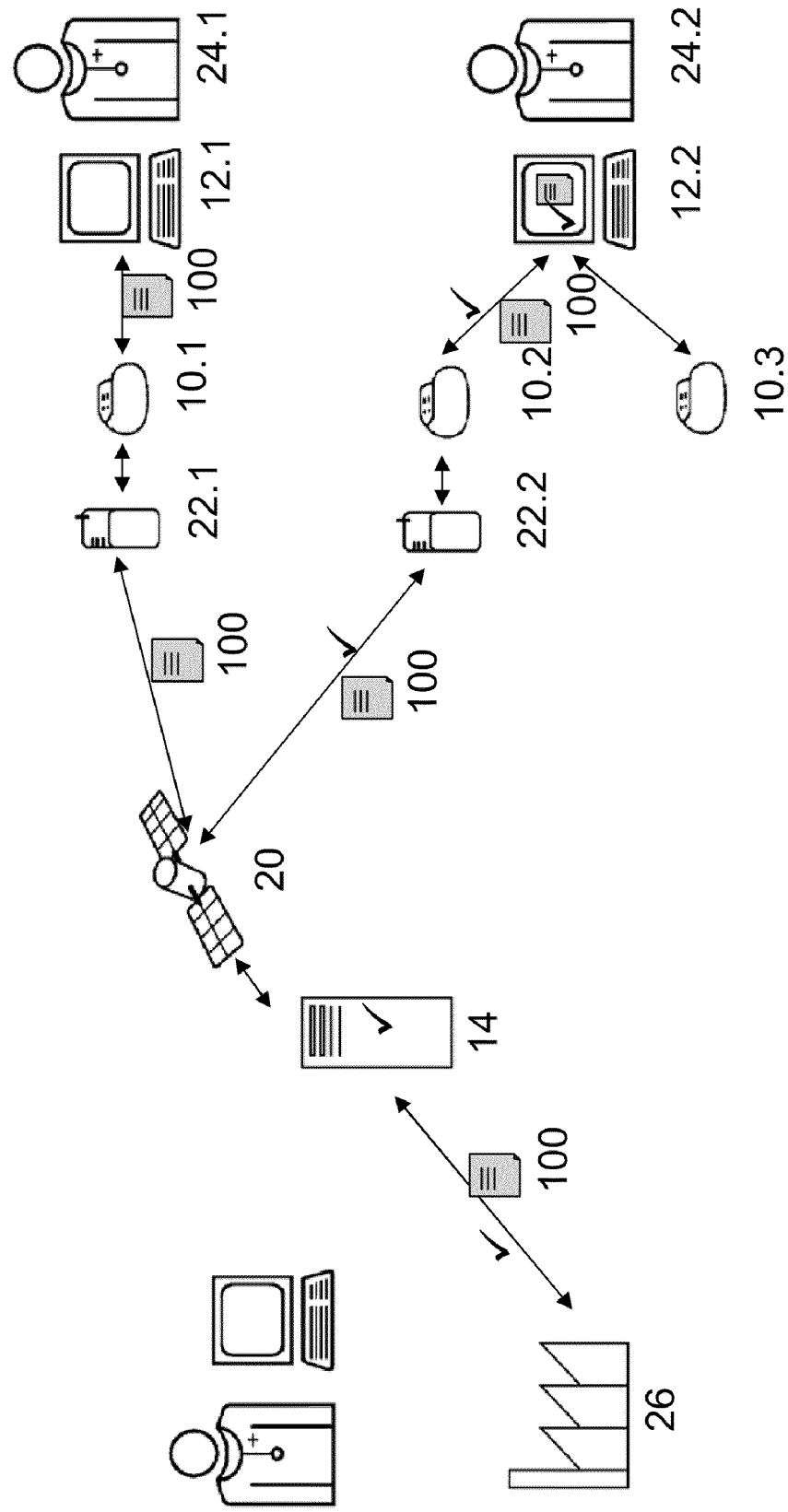
FIG. 7: shows the system from FIG. 1 in the case of distribution of a safety advisory by the manufacturer of the implant.

FIG. 7 illustrates the use of the system depicted in FIG. 1 for distribution of manufacturer information 100 to a follow-up care physician 24. Such manufacturer information 100, e.g., a product safety advisory, is placed on the server 14 by the manufacturer 26 of an implant 10, so that this information is sent to all electronic implants 10.1 and 10.2 connected to the server 14. In follow-up care for such an implant 10.1 and/or 10.2, this manufacturer information 100 is read out by the programming device 12 and saved on the programming device 12.

However, this manufacturer information 100 is displayed on the display 46 of the programming device 12 only when an implant 10.1 and/or 10.2 affected by this manufacturer information 100 is receiving follow-up care. Various implants 10 can receive follow-up care through one programming device 12.

It is also possible in this way to display on the programming device 12.2 manufacturer information 100 or other information for implants 10.3 which do not themselves have an interface for data communication with a central service center 14. This is depicted on the example of the implant 10.3. The manufacturer information 100 in FIG. 7 refers only to this implant 10.3 and is therefore displayed only when the implant 10.3 is receiving follow-up care but not another implant 10.1 or 10.2.

The programming device 12.2 may optionally be designed to acknowledge the follow-up care of an implant 10.3 plus display of the manufacturer information 100 by the fact that the control unit 42 (FIG. 3) of the programming device 12.2 generates a corresponding acknowledgement data packet 100, and this acknowledgement data packet 100 is sent back to the server 14 via the next implant 10.2 to which the programming device 12.2 is then connected and which has an interface 32 (FIG. 2) for bidirectional data communication with the central service center. To do so, first the acknowledgement data packet 100, which confirms the follow-up care of an implant 10.3, is saved in the programming device 12. Next this acknowledgement data packet 100 is transmitted from the programming device 12 to an implant 10.2 with an interface 32 for bidirectional data communication with the central service center. This implant 10.2 sends the acknowledgement data packet 100 with a next message over the corresponding patient device 22.2 and the satellite 20 to the server 14. The manufacturer 26 of the implant 10.3 can in this way perform a scan of the server 14 for follow-up care statistics for the implants 10 thereby affected. These follow-up care statistics may then include such implants 10.1 and 10.2 that have an interface 32 for bidirectional data communication with a central service center 14 as well as implants 10.3 that do not have such an interface 32 but instead have only an interface 30 for data communication with a programming device 12.

Figure 8:
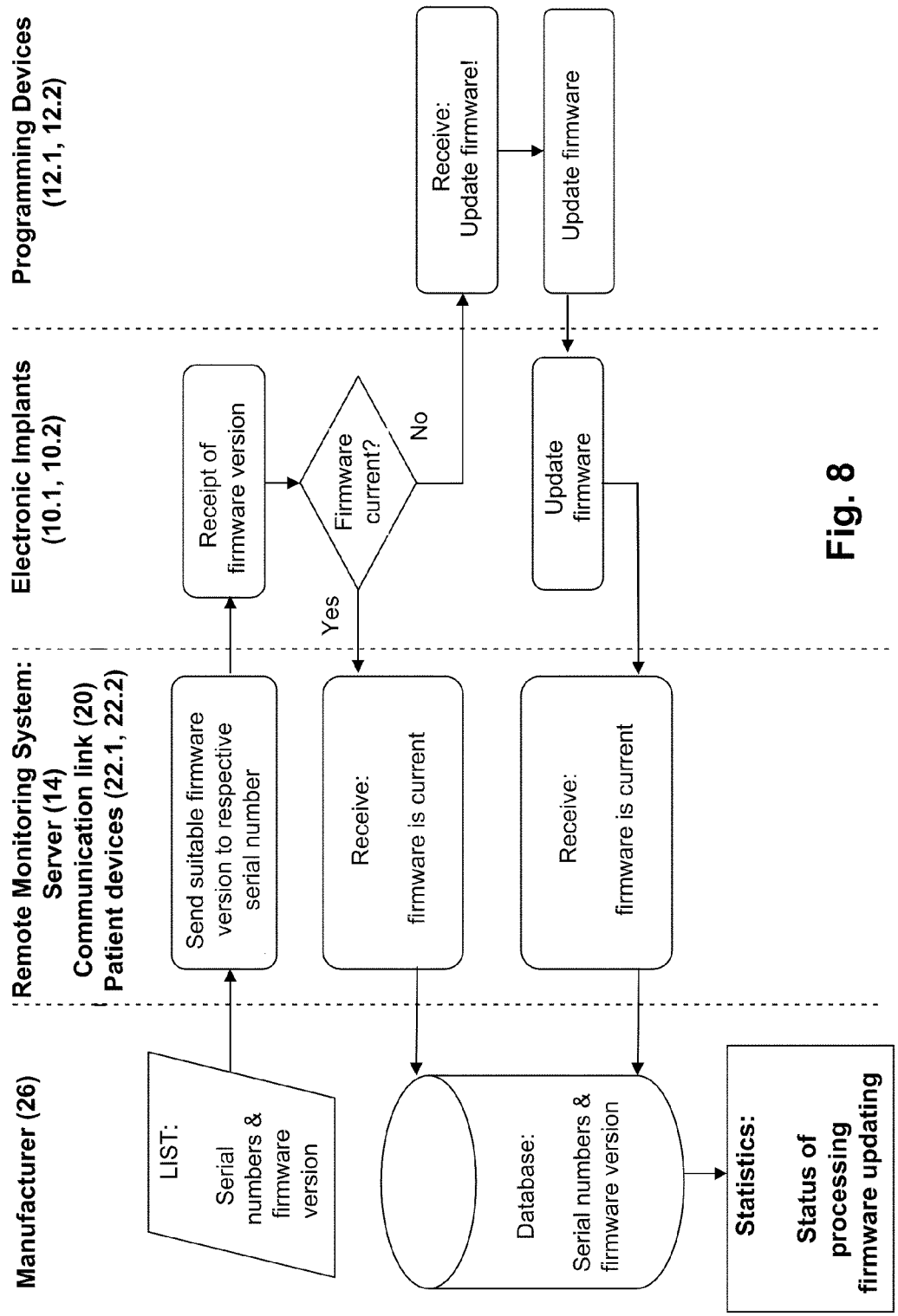
FIG. 8: shows the sequence in the event of a firmware update.

FIG. 8 shows the sequence for the case of a firmware update of individual electronic implants 10.

The manufacturer 26 of electronic implants 10 stores a list of serial numbers and the respective firmware version numbers in the server 14. This information is then transmitted from the server 14 over the communication link 20 and the patient device 22 to the respective affected electronic implant 10, so that information about which firmware is required by the manufacturer for this implant 10 is stored temporarily in the respective electronic implant 10. Alternatively, the entire serial number list plus firmware information may be sent to all electronic implants 10 and stored there.

The respective electronic implant 10 compares the desired version with the current firmware version. If they match, then an acknowledgement that the firmware of the respective implant 10 matches the desired firmware is sent to the server 14.

If the firmware version does not match, then in the next regular follow-up care, the information about the desired firmware version is read out by the programming device 12 and, based on this information, the firmware update process is initiated. If the firmware has been updated accordingly, the electronic implant 10 sends a corresponding acknowledgement to the server 14 with the next periodic message.

Acknowledgements of the successful firmware updates are then scanned by the manufacturer 26 in the server 14 and saved in a corresponding database. They may thus be analyzed statistically.

Figure 9:
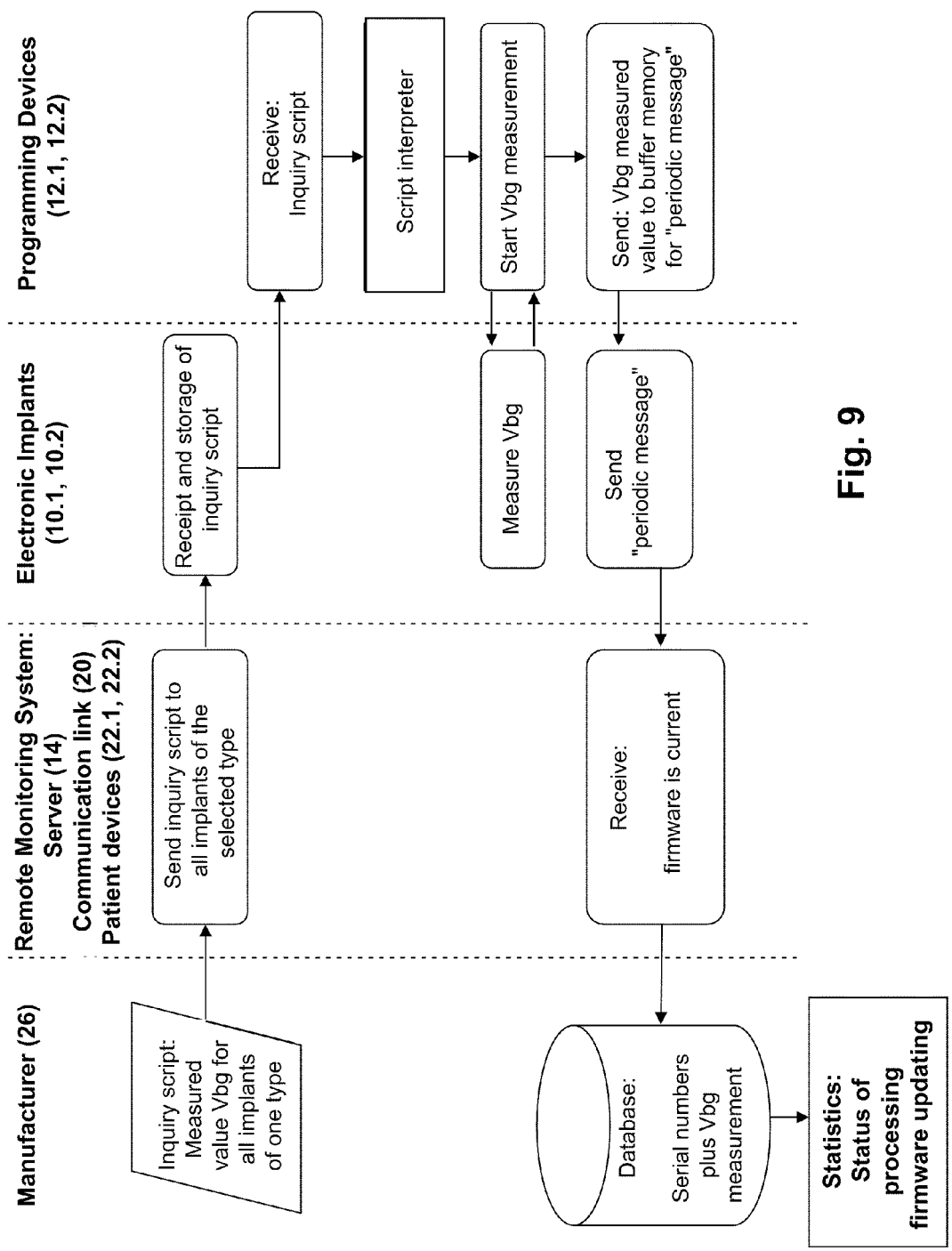
FIG. 9: shows the sequence in the event of control of a programming device component by a control command on the part of the central service center.

FIG. 9 shows the sequence of control of a programming device 12. In this case the manufacturer 26 of an implant 10 sends an inquiry to all implants 10 of a certain type, e.g., to inquire about a specific measured value such as the bandgap voltage Vbg for product monitoring. The manufacturer 26 sends a data packet with an interpretable script via the server 14, a satellite 20 and a patient device 22 to all affected electronic implants 10. This script is saved in the respective implant 10 and is read out by the programming device 12 in its follow-up care. The programming device software (i.e., the control unit 42 of the programming device 12) is expanded by a corresponding script interpreter in this exemplary version. This script interpreter converts the transmitted script for the bandgap voltage measurement into programming communication commands to trigger a bandgap measurement in the electronic implant 10 as part of the regular follow-up care. The corresponding measured value is read out by the programming device 12 after conclusion of the measurement and then is entered into the data transfer memory 36 of an implant 10, so that this measured bandgap voltage value is determined with the next regular data transmission from the electronic implant 10 the server 14. The manufacturer 26 of the implant 10 can scan these measured values on the server 14 and can analyze them statistically in a corresponding database.

The invention is not limited to the exemplary versions described above, and rather extends to all versions literally encompassed by the claims below, as well as to structurally and functionally equivalent versions.

What is claimed is:

1. A medical therapy method for use with a medical therapy system including:
   a. a central service center (14),
   b. a programming device (12) separate and spaced from the central service center (14); and
   c. a patient medical implant (10) separate and spaced from the central service center (14) and the programming device (12), the patient medical implant (10) having:
      (1) at least one interface (30, 32) configured to perform:

(a) a wireless data exchange with the programming device (12) over a first data communication channel, and
(b) a wireless data exchange with the central service center (14) over a second data communication channel, and
(2) a data memory (36),
the method including the steps of:
A. transmitting a center data packet from the central service center (14) over the second data communication channel, wherein the center data packet includes:
 I. messages and/or commands intended for the programming device (12);
 II. operational commands relating to one or more of:
  (A) the patient medical implant (10), and
  (B) a second medical implant (10.3), the second medical implant (10.3) being different from the patient medical implant (10.2), and wherein the patient medical implant (10) and the second medical implant (10.3) are in different patients;
B. receiving and storing the center data packet in the patient medical implant (10),
C. subsequently relaying at least a portion of the center data packet from the patient medical implant (10) to the programming device (12) via the first data communication channel,
D. transmitting any operational commands relating to the patient medical implant (10) from the programming device (12) to the patient medical implant (10), and
E. transmitting any operational commands relating to the second medical implant (10.3) from the programming device (12) to the second medical implant (10.3).

2. The method of claim 1 wherein the patient medical implant (10):
a. identifies any messages and/or commands within the center data packet which are intended for the programming device (12), and
b. relays to the programming device (12), via the first data communication channel, any of the messages and/or commands which are intended for the programming device (12).

3. The method of claim 1 wherein:
a. the center data packet includes a text message, and
b. the programming device (12) displays the text message on a display screen after receiving at least a portion of the center data packet.

4. The method of claim 1 wherein:
a. the center data packet includes commands, and
b. the programming device (12) executes the commands after receiving at least a portion of the center data packet.

5. The method of claim 4 wherein the programming device (12) adjusts the operation of the patient medical implant (10) in dependence on the executed commands.

6. The method of claim 1:
a. wherein the programming device (12) generates an acknowledgment data packet after receipt of at least a portion of the center data packet, and
b. further including the step of transmitting the acknowledgment data packet to the central service center (14).

7. The method of claim 1 further including the step of:
a. providing at least a portion of the center data packet to a physician (24) at the programming device (12);
b. transmitting a device data packet from the programming device (12) to the patient medical implant (10), the device data packet including a command developed at least partially in dependence on at least a portion of the center data packet;
c. executing the command in the patient medical implant (10).

8. The method of claim 1 further including the step of:
a. providing at least a portion of the center data packet to a physician (24) at the programming device (12);
b. transmitting a device data packet from the programming device (12) to the patient medical implant (10), the device data packet including a message developed at least partially in dependence on at least a portion of the center data packet;
c. subsequently transmitting at least the message of the device data packet to the central service center (14).

9. The method of claim 1 further including the step of transmitting an implant data packet from the patient medical implant (10) to the central service center (14) over the second data communication channel, the implant data packet including implant operation data and/or patient condition data.

10. The method of claim 9 wherein the central service center (14) generates the center data packet in dependence on the implant data packet.

11. The method of claim 1:
a. wherein the center data packet includes messages and/or commands relating to a second medical implant (10.3), the second medical implant (10.3) being different from the patient medical implant (10.2),
b. further including the step of transmitting the messages and/or commands from the programming device (12) to the second medical implant (10.3).

12. The method of claim 11 further including the steps of:
a. generating an acknowledgment data packet in the programming device (12) in response to the transmission of the messages and/or commands from the programming device (12) to the second medical implant (10.3);
b. transmitting the acknowledgment data packet to the central service center (14).

13. The method of claim 12 wherein the acknowledgment data packet is transmitted to the central service center (14) by first transmitting the acknowledgment data packet to at least one of:
a. the patient medical implant (10.2), and
b. a third medical implant (10.1), the third medical implant (10.1) being different from the patient medical implant (10.2) and the second medical implant (10.3),
followed by transmission to the central service center (14).

14. A medical therapy method for use with a medical therapy system including:
a. a central service center (14),
b. a programming device (12) separate and spaced from the central service center (14); and
c. a first medical implant (10.2) within a first patient, the first medical implant (10.2) being separate and spaced from the central service center (14) and the programming device (12),
d. a second medical implant (10.3) within a second patient, the second medical implant (10.2) being separate and spaced from the central service center (14) and the programming device (12), and being different from the first medical implant (10.2);
the method including the steps of:
i. transmitting a center data packet from the central service center (14) to the first and second medical implants (10.2, 10.3), the center data packet including commands for the operation of one or more of the first and second medical implants (10.2, 10.3);

ii. subsequently transmitting the center data packet from at least one of the first and second medical implants (10.2, 10.3) to the programming device (12);
iii. subsequently establishing communications between the programming device (12) and one of the first and second medical implants (10.2, 10.3); and
iv. transmitting to the communicating medical implant (10.2, 10.3) any of the commands for operation that relate to the communicating medical implant (10.2, 10.3).

15. The medical therapy method of claim 14 wherein: when communications are established between the programming device (12) and one of the first and second medical implants (10.2, 10.3), the one of the implants to which communications are established is not the implant that transmitted the center data packet to the programming device (12).

* * * * *